US00PP25738P3

(12) United States Plant Patent
Egger

(10) Patent No.: US PP25,738 P3
(45) Date of Patent: Jul. 21, 2015

(54) ×*HEUCHERELLA* PLANT NAMED 'GOLD CASCADE'

(50) Latin Name: ×*Heucherella* hybrid
Varietal Denomination: Gold Cascade

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 191 days.

(21) Appl. No.: 13/987,664

(22) Filed: Aug. 20, 2013

(65) Prior Publication Data

US 2015/0059037 P1 Feb. 26, 2015

(51) Int. Cl.
*A01H 5/12* (2006.01)

(52) U.S. Cl.
USPC ..... Plt./441

(58) Field of Classification Search
USPC ..... Plt./441
See application file for complete search history.

*Primary Examiner* — June Hwu
(74) *Attorney, Agent, or Firm* — Klarquist Sparkman, LLP

(57) ABSTRACT

A new and distinct ×*Heucherella* plant substantially as shown and described, characterized by gold leaves with reddish centers, reddish centers following the darker veins, a low dense trailing habit with good branching, medium size, ovate to orbicular leaves with shallow palmate lobing, and excellent vigor.

1 Drawing Sheet

Botanical denomination: ×*Heucherella* hybrid.

Variety designation: 'Gold Cascade'.

Cross reference to sibling: ×*Heucherella* 'Copper Cascade' (applied for concurrently, U.S. Plant patent application Ser. No. 13/987,660).

BACKGROUND OF THE INVENTION

The present invention relates to a new and distinct cultivar of ×*Heucherella* and given the cultivar name of 'Gold Cascade'. ×*Heucherella* is in the family Saxifragaceae. ×*Heucherella* 'Gold Cascade' originated from a controlled cross between *Heuchera* K521-1-1 (a proprietary unreleased *Heuchera*), as the seed parent, and *Tiarella* 42-2 (a proprietary unreleased *Tiarella*), as the pollen parent.

Compared to the seed parent *Heuchera* K521-1-1, the new cultivar is trailing with yellow leaves with red centers rather than clumping with pink to khaki leaves.

Compared to the pollen parent *Tiarella* 42-2, the new cultivar has gold leaves rather than green.

Compared to its sibling, ×*Heucherella* 'Copper Cascade', the new cultivar has gold foliage rather than red to rust.

Compared to ×*Heucherella* 'Yellowstone Falls', U.S. Plant Pat. No. 22,313, and ×*Heucherella* 'Sunrise Falls', U.S. Plant application Ser. No. 13/200,475, the new cultivar has a finer habit and stems, and with smaller leaves that are less lobed and have a stronger center pattern.

This new ×*Heucherella* is uniquely characterized by:

1. gold leaves with reddish centers,
2. reddish centers following the darker veins,
3. a low dense trailing habit with good branching,
4. medium size, ovate to orbicular leaves with shallow palmate lobing, and
5. excellent vigor.

This new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 6-month-old ×*Heucherella* 'Gold Cascade' in a 1 gallon pot in the shade house in June in Canby, Oreg.

FIG. 2 shows a close up of the flower.

DETAILED PLANT DESCRIPTION

The following is a detailed description of the new ×*Heucherella* cultivar based on observations of a six month-old specimens growing in a one gallon container in a cool greenhouse in March in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart*, 5$^{th}$ edition.

Plant:

*Form.*—Basal rosette with trailing stems, herbaceous perennial.

*Hardiness.*—USDA Zone 4 to 9.

*Size.*—23 cm tall from top of the foliage to the ground and 42 cm wide before trailing down.

*Habit.*—Mounding and trailing.

*Vigor.*—Excellent.

*Roots.*—Fibrous, freely branching, fine, and white in color.

Stem:

*Size.*—3 mm wide and grows to 80 cm long.

*Internode length.*—2.5 cm to 4.5 cm.

*Stem color.*—Greyed Purple 183C in sun and Yellow Green 148A tinted Greyed Purple 183C in shade.

Leaf:

*Type.*—Simple.

*Arrangement.*—Rosette and alternate.

*Shape.*—Broadly ovate to orbicular.

*Lobing/division.*—5 to 7 shallow palmate lobes.

*Venation.*—Palmate.

*Margins.*—Crenate.

*Apex.*—Mucronulate.

*Base.*—Cordate, usually overlapping.

*Blade size.*—Basal leaves grow to 7.5 cm long and 7 cm wide, stem leaves grow to 6 cm long and 5.5 cm wide.

*Surface texture.*—Glandular both surfaces.

*Petiole description.*—On basal leaf grows to 14 cm long and 1.5 mm wide, on stem grows to 11 cm long and 1.5 mm wide, both with glandular hairs and Greyed Purple 183C.

*Leaf color.*—Topside spring through winter leaves Yellow Green 145A with area around main veins Greyed Orange 177B and veins Greyed Purple 187A, bottom side Yellow Green 145A with dark center between Grey 201B and Greyed Purple 187A.

Inflorescence:

*Size.*—Usually 10 cm long and 2.5 cm wide, but grows to 18 cm long and 8.5 cm wide with branching.

*Type.*—Raceme. Number of flowers per raceme — about 30. Number of racemes — about 20 in first flush. Peduncle — grows to 19.5 cm long, 1.5 mm wide at base, 0 to 2 floral leaves (grow to 3.5 cm long and 3 cm wide, cupped, ovate, shallowly 3 lobed, tip mucronulate, margin crenate, glandular hairs on both sides, Yellow Green 145A on both sides, slight red markings near main veins Greyed Purple 187A), glandular hairs, Yellow Green 153A. Pedicel — grows to 6 mm long, with glandular hairs, Yellow Green 153A. Bloom period — May to July in Canby, Oreg.

Flower bud:

*Size.*—3 mm long and 2 mm wide.

*Description.*—Glandular puberulent, ovoid.

*Color.*—Greyed Yellow 161C.

Flower:

*Type.*—Imperfect.

*Shape.*—Stellate.

*Size.*—6 mm deep and 5 mm wide.

*Petal description.*—5 in number, sepal-like, oblanceolate, 2 mm long and 1.2 mm wide, tip obtuse, base attenuate, margin entire, glandular on both sides, Greyed Red 182C on both sides.

*Calyx description.*—2 mm deep and 5 mm wide, stellate, with 5 spreading lobes, divided ½ way to the base, oblong, glandular hairs on both sides, tip obtuse, margin entire, lobes Greyed Red 182C on both sides and base Yellow Green 145B.

*Stamen description.*—None.

*Pistil description.*—10 in number, grow to 5 mm long and 1.5 mm wide, ovaries grow to 3 mm long and 1.5 wide, Yellow Green 145B, beaked style 2 mm long Greyed Red 182C.

*Fragrance.*—None.

*Lastingness.*—Each raceme blooms for about 2 weeks on the plant.

*Flower attitude.*—Semi-outwards.

*Flowering stem attitude.*—Upright.

Fruit and seed: None.

Disease and pest tolerance: The new cultivar is typical to the genus. No known resistances to pests or diseases. No problems have been found in Canby, Oreg.

I claim:

1. A new and distinct ×*Heucherella* plant as herein illustrated and described.

* * * * *

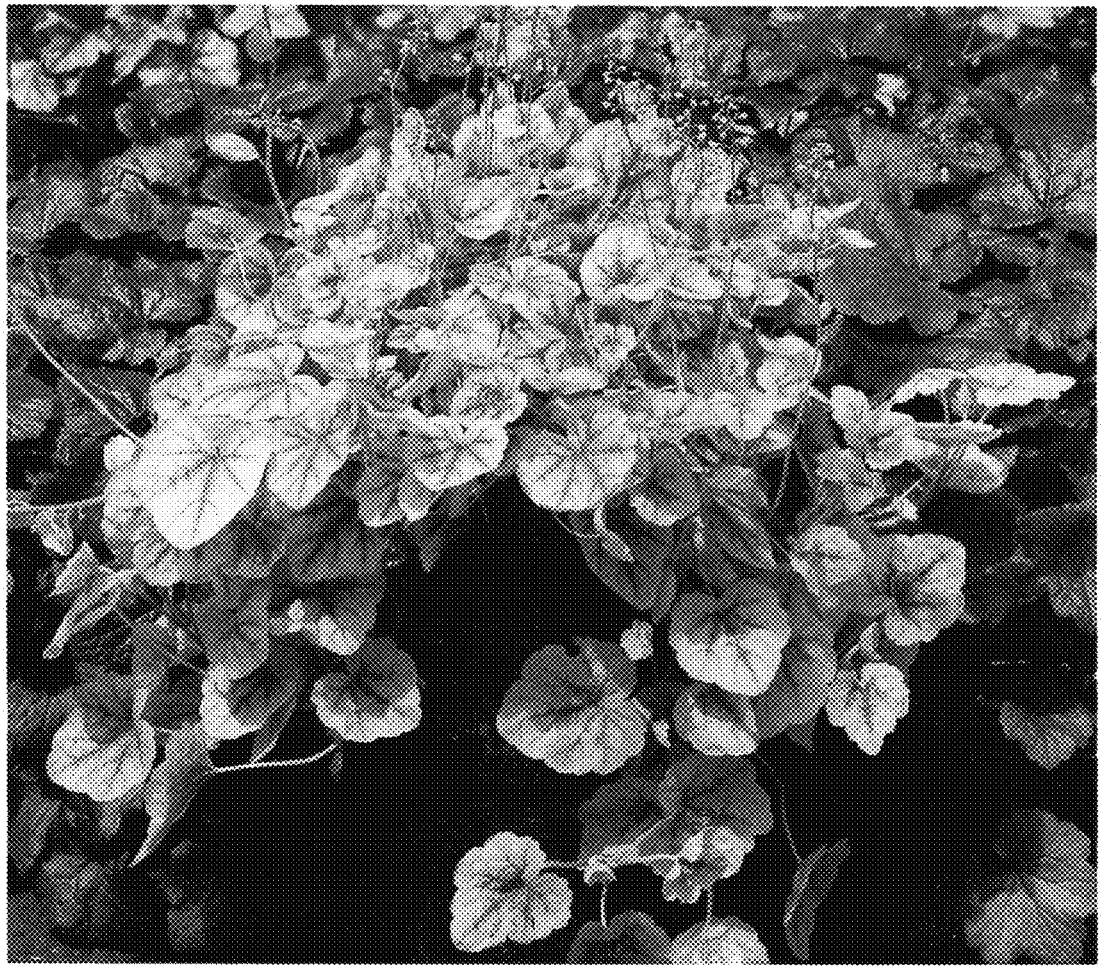
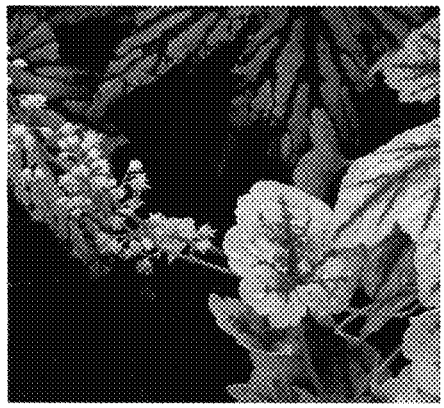
FIG. 1 above
FIG. 2 on left